(12) United States Patent
Grodzki et al.

(10) Patent No.: US 11,883,127 B2
(45) Date of Patent: Jan. 30, 2024

(54) METHOD AND MAGNETIC RESONANCE APPARATUS FOR SYNCHRONOUS IMAGING AND RADIATION THERAPY

(71) Applicant: Siemens Healthcare GmbH, Erlangen (DE)

(72) Inventors: David Grodzki, Erlangen (DE); Arne Hengerer, Möhrendorf (DE); Sebastian Schmidt, Weisendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 96 days.

(21) Appl. No.: 16/939,218

(22) Filed: Jul. 27, 2020

(65) Prior Publication Data
US 2020/0352442 A1 Nov. 12, 2020

Related U.S. Application Data

(63) Continuation of application No. 16/040,606, filed on Jul. 20, 2018, now abandoned.

(30) Foreign Application Priority Data

Jul. 21, 2017 (DE) ...................... 10 2017 212 553.5

(51) Int. Cl.
*A61B 5/00* (2006.01)
*G01R 33/48* (2006.01)
(Continued)

(52) U.S. Cl.
CPC ............ *A61B 5/0036* (2018.08); *A61B 5/055* (2013.01); *A61B 5/7207* (2013.01);
(Continued)

(58) Field of Classification Search
CPC ..... A61B 5/0036; A61B 5/055; A61B 5/7207; G01R 33/4812; G01R 33/4808;
(Continued)

(56) References Cited

U.S. PATENT DOCUMENTS 6,198,957 B1  3/2001 Green
6,385,286 B1 * 5/2002 Fitchard ............... A61N 5/1042
378/65

(Continued)

OTHER PUBLICATIONS

German Office Action dated May 24, 2019, for Application No. 10 2017 212 553.5, and English translation.
(Continued)

*Primary Examiner* — Patricia J Park
*Assistant Examiner* — Adil Partap S Virk
(74) *Attorney, Agent, or Firm* — Banner & Witcoff Ltd.

(57) ABSTRACT

In a method for synchronous magnetic resonance (MR) imaging and radiation therapy using a combined system having a radiation apparatus and an MR imaging apparatus, wherein the system is designed to record MR signals of a subject during irradiation of the subject, a three-dimensional MR volume data set of the subject is acquired that contains a target volume for the irradiation, the location of a central beam of the radiation therapy apparatus relative to the subject, is continuously determined, and a second MR image data set is determined, which is positioned essentially perpendicular to the central beam. If the location of the central beam changes, a correspondingly changed second MR image data set is determined perpendicular to the central beam.

16 Claims, 4 Drawing Sheets

(51) Int. Cl.
*A61B 5/055* (2006.01)
*A61N 5/10* (2006.01)

(52) U.S. Cl.
CPC ......... *A61N 5/1049* (2013.01); *A61N 5/1071* (2013.01); *G01R 33/4808* (2013.01); *A61N 5/1067* (2013.01); *A61N 2005/1055* (2013.01); *A61N 2005/1059* (2013.01); *G01R 33/4812* (2013.01)

(58) Field of Classification Search
CPC .. A61N 5/1049; A61N 5/1071; A61N 5/1067; A61N 2005/1055; A61N 2005/1059
See application file for complete search history.

(56) References Cited

U.S. PATENT DOCUMENTS

| | | | | |
|---|---|---|---|---|
| 2004/0254492 | A1* | 12/2004 | Zhang | A61B 5/1135 600/534 |
| 2005/0197564 | A1 | 9/2005 | Dempsey | |
| 2006/0122502 | A1* | 6/2006 | Scherch | A61N 5/1049 600/426 |
| 2008/0049896 | A1 | 2/2008 | Kuduvalli | |
| 2010/0274120 | A1* | 10/2010 | Heuscher | A61B 6/032 600/424 |
| 2013/0090547 | A1* | 4/2013 | Bani-Hashemi | A61N 5/1039 600/411 |
| 2013/0217994 | A1* | 8/2013 | Kim | A61B 5/4244 600/407 |
| 2014/0192046 | A1* | 7/2014 | Paragios | G06T 15/005 345/419 |
| 2014/0286556 | A1* | 9/2014 | Fouras | A61B 6/481 382/131 |
| 2015/0209600 | A1* | 7/2015 | Overweg | A61B 5/055 600/1 |
| 2016/0213947 | A1* | 7/2016 | Han | A61N 5/1037 |
| 2017/0050051 | A1* | 2/2017 | Berbeci | A61N 5/1067 |
| 2017/0360325 | A1* | 12/2017 | Hebert | G01R 33/4808 |
| 2017/0361128 | A1* | 12/2017 | Lachaine | G16H 30/20 |
| 2019/0021600 | A1 | 1/2019 | Grodzki et al. | |

OTHER PUBLICATIONS

Decision to Grant dated Nov. 11, 2019, for Application No. 10 2017 212 553.5, and English translation.

* cited by examiner

METHOD AND MAGNETIC RESONANCE APPARATUS FOR SYNCHRONOUS IMAGING AND RADIATION THERAPY

CROSS-REFERENCE TO RELATED APPLICATIONS

The present application is a continuation of U.S. patent application Ser. No. 16/040,606, filed on Jul. 20, 2018, which claims foreign priority to German patent application no. 10 2017 212 553.5, filed on Jul. 21, 2017, the contents of each which are incorporated herein by reference in their entireties.

FIELD OF THE INVENTION

The present invention concerns a method for controlling a combined system that includes a radiation therapy apparatus and a magnetic resonance imaging apparatus, as well as such a combined system, and a non-transitory electronically readable data storage medium that implement such a method.

DESCRIPTION OF THE PRIOR ART

Radiation therapy for treating cancerous pathologies is well known, wherein accelerated particles are directed onto a subject such that their energy is deposited primarily in a target volume, e.g. the tumor. An important point when planning radiation therapy treatment is to hit the target volume and the tumor present therein as precisely as possible and to expose healthy tissue to the radiation as little possible. Image data of the subject can be used to plan the irradiation.

The target volumes are sometimes susceptible to movement, possibly caused by respiratory movement of the subject or intestinal movement, and it is therefore challenging to minimize exposure of healthy tissue or organs during the irradiation, and to control the beam such that the target volume is reached.

Radiation therapy facilities are known that, for example, allow images of the irradiated body parts to be produced during the irradiation. Such a system is described in U.S. Pat. No. 6,198,957, for example.

Conventional radiation therapy facilities do not allow the radiation exposure of at-risk organs to be detected in real time. In a known methodology, the dose distribution is planned prior to the radiation therapy on the basis of image data that were acquired in advance of the treatment, such that a specific region of interest (ROI) receives the lowest possible total dose.

SUMMARY OF THE INVENTION

An object of the present invention is to improve the calculation of the radiation exposure of the irradiated tissue.

According to a first aspect of the invention, a method is provided for controlling a combined system that has a radiation therapy apparatus and an MR imaging apparatus, the system being designed to record MR signals of a subject during irradiation of the subject. In the method, a three-dimensional MR volume data set of the subject is acquired, which contains a target volume for the irradiation. The location of a central beam of the radiation therapy apparatus relative to the subject is continuously determined. A second MR image data set is determined that is oriented essentially perpendicularly to the central beam wherein, if the location of the central beam changes, a correspondingly changed second MR image data set is determined perpendicular to the central beam.

By virtue of the position of the central beam of the irradiation being determined continuously, the second MR image data set can be adapted essentially synchronously therewith, such that it lies perpendicular to the central beam. The second MR image data set continues to include the region of the subject that is irradiated by the central beam. This means that MR image data of the irradiated region is available continuously, and therefore such image data can be used to calculate the dose distribution in the irradiated tissue.

The changed second MR image data set can be an MR image data set that is recorded in a volume during the irradiation of the subject wherein, if the location of the central beam changes, the changed MR image data set is recorded so that a changed volume of the MR image data set lies perpendicular to the central beam.

Because the position of the central beam of the irradiation is determined continuously, the recording volume for the second MR image data set can be adapted synchronously therewith, and MR signals can be recorded in a recording volume that is perpendicular to the central beam.

In this context, the second MR image data set is preferably determined such that it contains a portion of the target volume. The target volume encompasses the region to be irradiated, i.e., the tumor. When the MR recording volume contains the target volume, it is possible to calculate the radiation dose in the target volume using the MR image data that have been produced.

In addition to the target volume, the MR recording volume can be so determined as to include specific anatomical regions such as at-at-risk organs, for example. It is thereby possible to calculate the radiation exposure for the at-at-risk organs from the MR data that have been produced.

Furthermore, the three-dimensional MR volume data set of the subject can be recorded prior to the irradiation. The three-dimensional MR volume data set is compared with the second MR image data set and any transformation of the irradiated tissue between the recording of the volume data set and the second MR image data set is determined. With the use of this transformation, it is then possible to calculate a deformed three-dimensional MR volume data set that takes into account any possible movement between the recording of the data sets. The deformed three-dimensional MR volume data set can then be used, inter alia, for the dose calculation. This is particularly advantageous if prior to the irradiation, a volume data set was acquired that had a higher spatial resolution or a particularly favorable contrast. This is possible because the recording prior to the irradiation need not take place in real time, and therefore more time is available for measurement. This procedure can also be advantageous if only one or a few slices are captured during the irradiation.

The second MR image data set is preferably selected such that it includes only a partial region of the three-dimensional MR volume data set, such that the MR image data can be recorded with higher temporal resolution. An MR system is not usually capable of depicting a complete volume with a high temporal resolution, which is necessary in order to follow the movement of the central beam. The MR image data is therefore recorded e.g. in a number of two-dimensional slices (e.g. between five and ten slices) which then are perpendicular to the central beam. Such MR image data can be recorded in a temporal resolution which is sufficient for the purpose of following a central beam, e.g. with a frequency of between 0.5 and 5 Hertz.

A transformation and a deformed MR volume data set can then be calculated in each case for the changed locations of the central beam, so that it is possible to trace which if any at-risk organs lie in the beam path or how the target volume lies relative to the beam.

The radiation dose that is determined with the aid of the MR image data can likewise be used to control the irradiation, wherein for example in the event that a limit dose is exceeded in a defined anatomical region such as specific at-risk organs or other tissue outside the target volume or in the target volume, the irradiation can be switched off automatically.

The location of the central beam can be determined e.g. with the aid of control data which is used to control the radiation in the radiation therapy apparatus. It is likewise possible to determine the location of the central beam with the aid of image data, said image data being recorded by a camera which monitors the position of the central beam. It is also possible to apply defined markings to the subject, wherein said markings can then be identified in the MR image data and have a defined location relative to the central beam and therefore the location of the central beam can be inferred when the defined markings are identified.

In a further embodiment, the second MR image data set is calculated on the basis of the MR volume data set and the detected movement information only. The additional movement information can come from a movement sensor such as a respiration sensor, for example. It is thereby possible additionally to determine the movement information of the subject, the movement information and the dimensional MR volume data set being used to calculate the second MR image data set. The transformation can be calculated from the three-dimensional MR volume data set and the movement information, a deformed second MR image data set being calculated from the second MR image data set and the deformation. The deformed second MR image data can contain a number of two-dimensional slices, wherein the deformed three-dimensional volume data set is calculated using the deformed second MR image data set and the three-dimensional MR volume data set.

The invention also encompasses a combined system having the radiation therapy apparatus and the MR imaging apparatus, wherein the combined system has a control computer that controls the radiation therapy apparatus and the MR imaging apparatus, and has a memory, wherein the memory stores information that are executed by the control computer. The system is designed to execute the method as described above and in further detail below when the control information is executed in the control computer.

The present invention also encompasses a non-transitory, computer-readable data storage medium encoded with programming instructions (program code) that, when the storage medium is loaded into a control computer of a combined system having a radiation therapy apparatus and a magnetic resonance imaging apparatus, cause the control computer to operate the combined system so as to implement any or all embodiments of the method according to the invention, as described above.

The features described above and the features described below can be used not only in the explicitly stated combination, but can also be combined in other ways unless explicitly mentioned otherwise.

DESCRIPTION OF THE PREFERRED EMBODIMENTS

The present invention is explained in greater detail below on the basis of preferred embodiments with reference to the drawings. Identical reference symbols in the figures designate identical or similar elements. Furthermore, the figures are schematic illustrations of various embodiments of the invention. The elements illustrated in the figures are not necessarily true-to-scale, the illustrated elements instead are represented so as to make the function and the purpose of the elements comprehensible to those skilled in the art. The connections as illustrated in the figures between functional units or other units can also be implemented as indirect connections which may be wireless or hard-wired. Functional elements can be implemented as hardware, software, or a combination of hardware and software.

Figure 1:
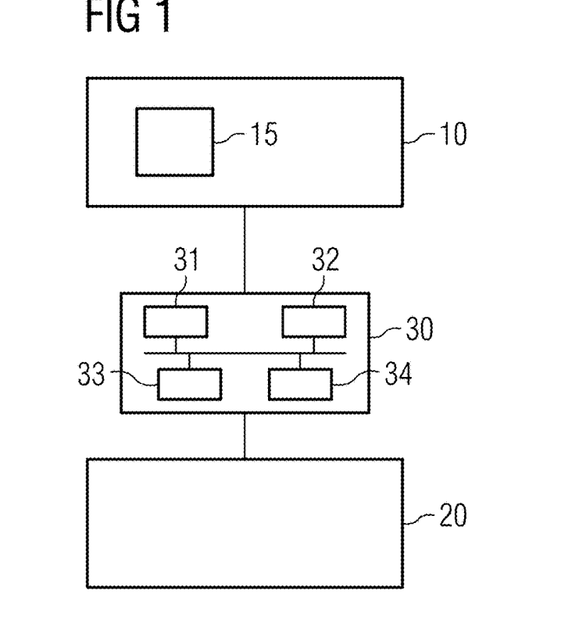
FIG. 1 schematically shows a combined system having a radiation therapy apparatus and an MR imaging apparatus, the system being designed to synchronize the MR imaging with the central radiation beam.
Figure 2:
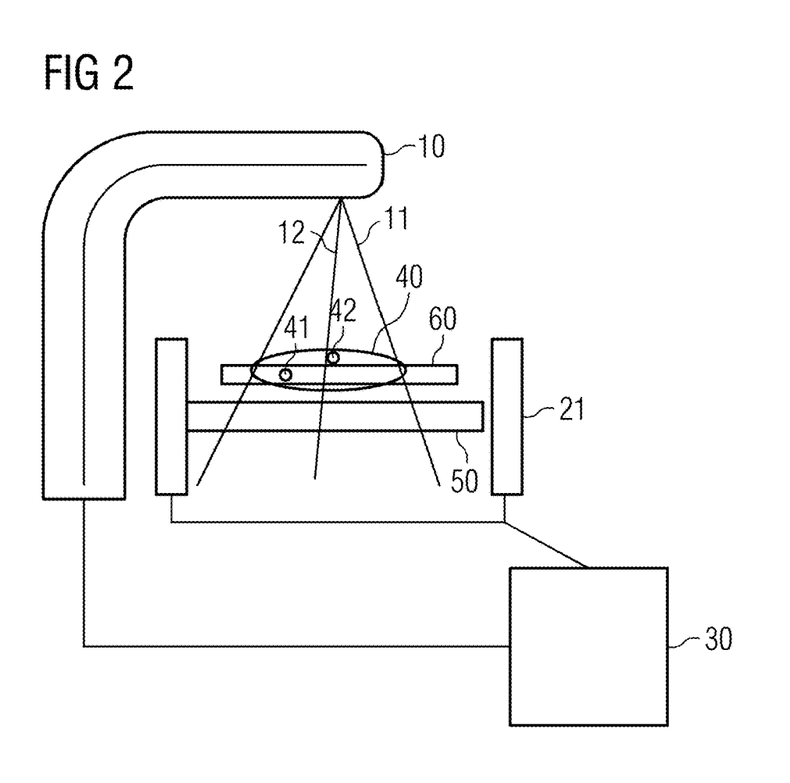
FIG. 2 schematically shows an embodiment of the combined system with further details.

Schematically illustrated in FIG. 1 is a combined system having a radiation therapy apparatus 10, an MR imaging apparatus 20, and a central control computer 30. The radiation therapy apparatus 10 has at least one beam source 15 that generates a therapeutic beam. The therapeutic beam can be an x-ray beam or a particle beam, e.g. an electron beam. As shown in FIG. 2, the beam source generates the therapeutic beam 11 with a specific distribution, the beam having a central beam 12. The beam is shaped by a collimator and therefore, if the collimator assumes a round shape, has e.g. the shape of a cone with the beam source at its tip. The central beam is then the symmetry axis of the cone. The radiation therapy apparatus 10 also has elements that are not shown, e.g. a drive motor for controlling the positioning of the beam and further components that are required for the generation and positioning of the generated photon beam or particle beam.

The MR imaging apparatus 20 is designed to generate MR images of the subject. As usual, the MR imaging apparatus has a magnet that produces a polarization field BO, wherein magnetic resonance signals are recorded from a subject 40 on a bed 50. By directing radio-frequency pulses and switching magnetic field gradients, the magnetization generated by the polarization field BO is deflected from the position of equilibrium and spatially encoded, and the resulting magnetizations are detected. The manner in which MR images can be generated by directing the RF pulses and switching the magnetic field gradients in different combinations and sequences is known in principle to those skilled in the art, and so need not be explained in further detail herein.

The combined system also has a control computer 30 that controls the combined system. The control computer 30 controls the MR imaging apparatus and to control the radiation therapy facility, but the radiation therapy apparatus 10 and the MR imaging apparatus 20 may also have other control computers that are monitored by the central control computer 30. The control computer 30 has a processor 31 composed of one or more processor circuits. A memory 32 stores program modules or programs that implement the operation of the combined system when executed by the processor 31. An input unit 33 and a display unit 34 are also provided via which inputs can be entered and the generated MR image data can be visually presented. An operator can control the combined system via the input unit 33. The combined system can have further functional units which, for clarity, are not illustrated. For example, an interface can be provided via which data can be read into the system from outside, e.g. data from a camera that detects the central beam of the radiation therapy apparatus 10. The interface can also receive data from other sensors, such as a movement sensor, e.g. a respiration sensor, by which the respiratory movement or other movement of the subject is detected.

FIG. 2 schematically shows an embodiment of the combined system having the radiation therapy apparatus 10 and a gradient coil system 21 of the MR imaging apparatus 20. The generated therapeutic beam 11 has a central beam 12 that passes through the subject 40, the target volume 41 being illustrated schematically with an at-risk organ 42, which must be affected as little as possible by the radiation. The subject 40 is on a bed 50.

In order to determine as effectively as possible the radiation exposure of moving at-at-risk organs, it is desirable for the MR imaging plane, i.e. the MR recording volume, to move synchronously and in real time with the beam source of the radiation therapy apparatus 10, thereby making it possible at all times to identify whether and for how long specific structures are situated in the beam path.

According to the invention, the combined system shown in FIG. 1 is now able to determine an MR recording volume during the irradiation, such that images of one or more slices are generated during the irradiation, said slices lying perpendicular to the central beam 12 of the therapeutic beam 11 of the radiation therapy apparatus 10, wherein the recording volume follows the movement of the central beam when the position thereof changes. In this context, an MR recording volume 60 is preferably defined automatically such that the volume at least partly contains or intersects one or a number of at-at-risk organs and/or the target volume of the irradiation.

In order to achieve this, the control computer 30 receives information relating to the location of the central beam 12 of the radiation therapy apparatus 10. This information can come from the control computer of the linear accelerator, for example, or from a previously defined therapy plan that controls the radiation therapy apparatus 10, or be generated by sensors such as a camera that monitors the apparatus 10, for example. On the basis of this information and on the basis of the information relating to the location of the target volume and/or the at-risk organs that were marked in a pre-prepared data set, MR images are calculated. The control of instructions for the MR imaging apparatus 20 is effected such that the slices in the subject are defined so as to be perpendicular to the central beam 12 and preferably include at least partly certain anatomical regions such as e.g. at-risk organs or the target volume at all times during the recording. Using image post-processing techniques, the generated MR images can be post-processed for the purpose of identifying individual anatomical regions in the MR images, such that on the basis of the object identification and the knowledge of the at-risk organs and/or target volumes, the MR system can be controlled such that the recording volume is correctly positioned. In particular, the gradient systems of the MR imaging apparatus 20, which are responsible for the positioning and location of the acquired measured slices, are controlled for this purpose.

An example of a method that can be performed using the combined system in FIG. 1 is as follows:

In a first step, a three-dimensional MR data set of the target volume is acquired before the radiation treatment.

In a second step, the at-risk organs 42 and the target volume 41 are then identified and e.g. marked in the three-dimensional data set.

In a third step, the position of the beam source of the radiation therapy apparatus 10 is determined, e.g. with the use of a three-dimensional camera or with the use of data that are immediately available in the radiation therapy apparatus 10, e.g. the control data for controlling the beam path. This means that the radiation therapy is started after the first two steps. A further possibility for determining the position of the central beam, e.g. in the case of an open magnet, is to use a metal antenna in addition to the collimator, the metal antenna being aligned parallel with the beam and generating an artifact which represents the beam path with a known offset in the MR images that are generated.

The positions of the central beam 12 are determined continuously and two-dimensional MR data sets are generated which lie perpendicular to the central beam 12 and pass through the at-risk organs and/or the target volume. Rapid MR pulse sequences are suitable here, e.g. using steady-state (TruFISP) or quarter-Fourier (HASTE) techniques. Such MR sequences can record a slice in a few tenths of a second, depending on the resolution. Steady-state sequences are advantageous in this case, particularly with low-field systems of less than 1 Tesla.

In a further step, this two-dimensional MR image data are used to monitor the radiation therapy, e.g. in order to determine the dose for the tissue around the target volume, in particular in at-risk organs. Moreover, it is thereby possible to determine the dose in the target volume itself. The manner in which the radiation dose can be inferred from knowledge of the tissue and the tissue components represented in the MR image data is known to those skilled in the art. Provision is typically made for continuously segmenting the risk organ and calculating the attenuation of the tissue in the beam path and the energy absorption in the organ itself. In this case, the physical properties of the corresponding tissue can be determined from the MR image or stored beforehand in a database.

Figure 3:
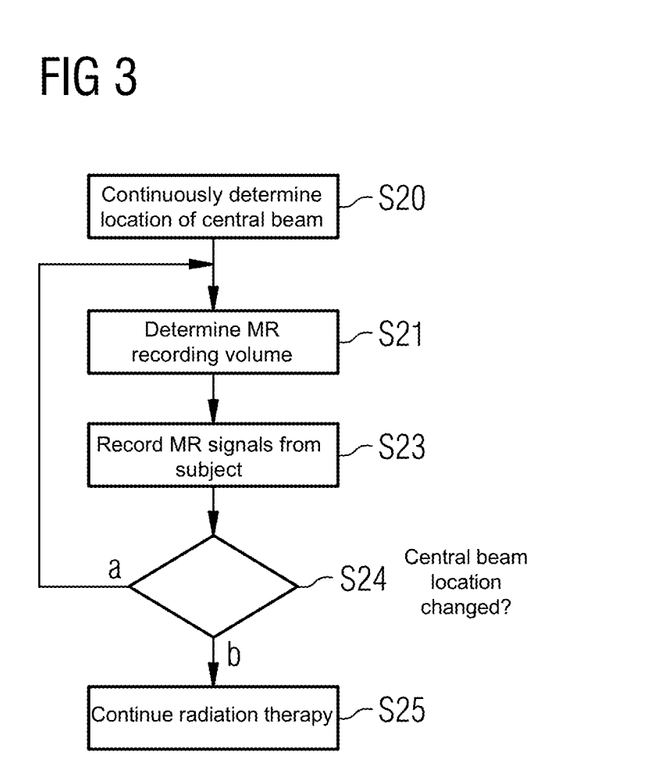
FIG. 3 shows a flowchart with steps that can be executed during the synchronization of the MR imaging with the central beam.

FIG. 3 schematically illustrates a method having some of the steps that can be performed by the combined system. In a step S20, the continuous determination of the location of the central beam 12 relative to the subject 40 takes place. In a step S21, the MR recording volume for the creation of the MR image data is then determined such that the MR recording volume, preferably in the form of one or more two-dimensional slices, is positioned perpendicular to the central beam 12. In a step S23, the recording of the MR signals from the subject in the determined MR recording volume then takes place for the production of the MR image data. In the step S24, it is checked whether the location of the central beam 12 has changed. If this is the case as indicated by letter A, a changed MR recording volume is determined correspondingly, perpendicular to the location of the central beam 12, and in the step S23 the MR slice images are generated repeatedly for the changed recording volume. If the location of the central beam 12 does not change or changes less than a limit value, the method can be continued as indicated by B with step S25, in which e.g. the radiation therapy is continued until a desired dose has been applied in the target volume 41 or the method is ended when a desired dose has been reached.

Figure 4:
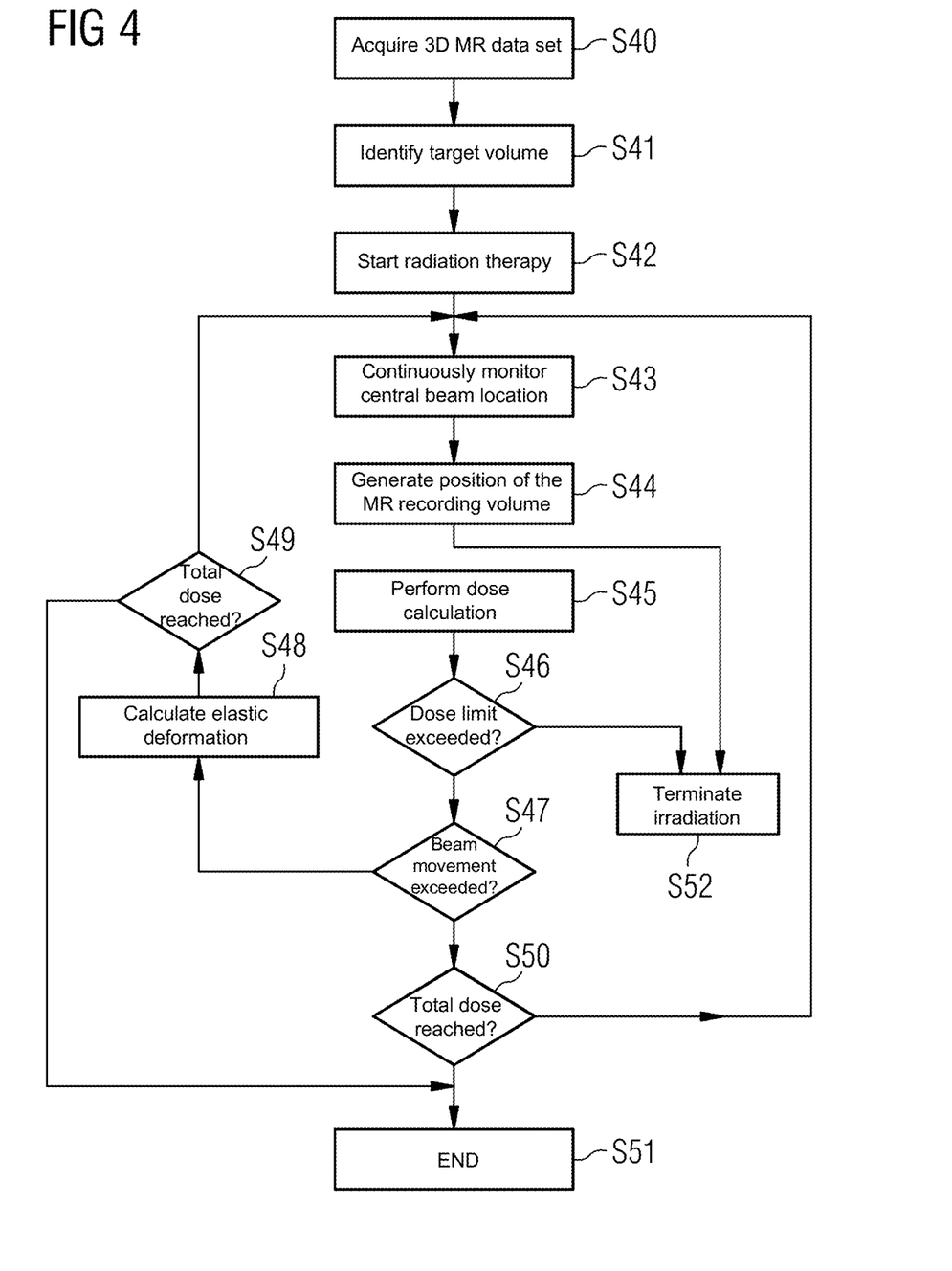
FIG. 4 shows a further flowchart of an embodiment variant comprising steps which are executed during the synchronization of the MR imaging with the central beam.

FIG. 4 shows a further method with steps which can be performed by the combined system. In a step S40, a three-dimensional MR data set is acquired from the target volume prior to the radiation treatment. In a step S41 the target volume and possible at-risk organs or other risk anatomy are identified, e.g. by segmentation, and these can then also be marked in color in the MR images shown. In a step S42, the radiation therapy is started and the location of the central beam 12 is continuously monitored in a step S43. With the knowledge of the location of the central beam 12, it is then possible in step S44 to generate the position of the MR recording volume, e.g. the number of two-dimensional slices. In particular, the recorded MR images of the MR recording volume have a temporal resolution of less than 1 or 2 seconds. Depending on the irradiation plan, the MR recording volume can also be recorded using recording techniques other than a number of two-dimensional slices, as long as the temporal resolution is sufficient, e.g. radial undersampled three-dimensional recording techniques can be used.

In a step S45, the dose calculation then takes place for the target volume and the surrounding tissue, which may contain one or more at-risk organs. In a step S46, it is checked whether a dose limit has been exceeded in one of the monitored tissues. If this is the case, the irradiation is terminated in step S52. If this is not the case, it is checked in step S47 whether the movement of the central beam 12 has exceeded a limit value, such that a recalculation of the MR recording volume appears to be necessary. If this is the case, it is possible in a step S48 to compare the volume data set originally generated in the step S40 with the MR data recorded in step S44, in order to calculate an elastic deformation of the volume data set before the position of the central beam 12 is determined again and the MR measurement in the MR recording volume is repeated in the changed recording volume. This is particularly beneficial if the data set captured in step S40 has a higher resolution or better contrast than the data set or data sets captured during the irradiation.

It can first be checked in a step S49 whether the total dose has already been reached. If this is not the case, irradiation continues and the position of the central beam 12 continues to be determined. However, if the total dose has been reached, the method can be ended in a step S51. If no movement of the central beam 12 was identified in the step S47, it is further checked whether the total dose has been reached in step S49. If this is not the case, the method is continued with the determination of the location of the central beam in step S43. When the total dose is reached in step S50, the method ends in step S51.

For example, the current dose in the MR recording volumes that were calculated in step S44 can be calculated and displayed in real time, e.g. in a false-color illustration. The MR image data of the MR recording volume from step S44 can serve as a basis for the dose calculation, wherein this dose calculation can be used in turn to control the radiation therapy apparatus 10, e.g. to switch off if a limit dose for a specific tissue region has been exceeded as explained inter alia in step S46.

Figure 5:
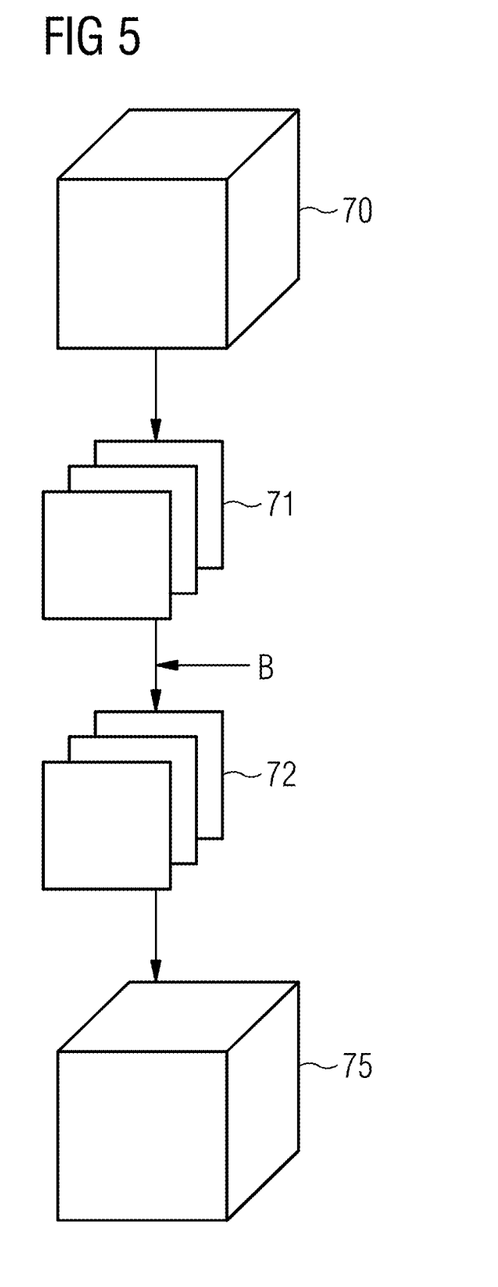
FIG. 5 shows an embodiment in which the second MR image data set is calculated with the use of movement information.

In the exemplary embodiment cited above, the second MR image data set was generated by recording MR signals such that the second MR image data set is recorded while the therapeutic beam moves. In the embodiment variant described below, the second MR image data set is calculated on the basis of additionally recorded movement information and on the basis of MR volume data recorded at the outset. In this context, only the three-dimensional volume data set is generated initially and the further two-dimensional data sets are only calculated by computing two-dimensional slices from the initial three-dimensional volume data as a result of reformatting, the two-dimensional slices being elastically deformed on the basis of the movement information. Data from further sensors such as a respiratory sensor can be used for this elastic deformation.

FIG. 5 shows the three-dimensional volume data set 70 being recorded at the outset as in the foregoing example. A number of two-dimensional slices 71 are then computed from the volume data set 70, the calculation taking place such that the slices 71 lie perpendicular to the central beam. These slices form the second MR image data set. The movement of the subject is monitored continuously by external movement sensors such as a respiratory belt or cameras, for example, the sensors providing movement information B as indicated in FIG. 5. This movement information B is used to determine the deformed second MR image data set 72. This lies perpendicular to the central beam 12 and takes into account the actual movement of the subject during the irradiation. Using the deformed second MR image data set, it is then again possible to determine the deformed three-dimensional MR volume data set 75, this consisting of a portion of the volume data set 70, which portion was not replaced by the second MR image data set, and of the second MR image data set 72. By virtue of the continuously determined movement information, it is again possible to generate a plurality of volume data sets as in the other embodiment variant.

In summary, the combined system described above makes it possible to represent moving target volumes or at-risk organs, such that the control computer of the radiation therapy apparatus 10 can be adapted correspondingly. It is thereby possible during the irradiation to take e.g. movement data which is conditioned by the respiration or heartbeat into account.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for controlling a combined system comprising a radiation therapy apparatus and a magnetic resonance (MR) imaging apparatus, the method comprising:

acquiring, via the combined system, a three-dimensional MR volume data set prior to irradiation of the subject, the three-dimensional MR volume data set containing a target volume for irradiation of the subject with a radiation beam;

determining, via the combined system, movement information of the subject;

continuously determining, via the combined system, a location of a central beam of the radiation beam relative to the subject;

determining, via the combined system, that the location of the central beam has changed during the irradiation of the subject;

calculating, via the combined system, during the irradiation of the subject, an MR image data set comprising two-dimensional MR slices that are positioned substantially perpendicular to the central beam;

in response to the determination that the location of the central beam has changed, calculating, via the combined system during the irradiation of the subject, a changed MR image data set comprising two-dimensional MR slices that are substantially perpendicular to the central beam, wherein the MR image data set and the changed MR image data set are each respectively calculated, during the irradiation of the subject, without using a recorded MR data set in addition to the three-dimensional MR volume data set that was acquired prior to the irradiation of the subject by (i) using the movement information, and (ii) calculating, from the three-dimensional MR volume data set acquired prior to the irradiation of the subject, the two-dimensional MR slices of the changed MR image data set;

determining a radiation dose for the irradiation in predetermined regions of the subject using the MR image data set and the changed MR image data set; and controlling the irradiation using the determined radiation dose.

2. The method as claimed in claim 1, wherein calculating the MR image data set comprises calculating the MR image data set so as to at least partially contain the target volume for irradiation with the radiation beam.

3. The method as claimed in claim 1, comprising:
calculating a transformation of movement between the recording of the three-dimensional MR volume data set and the calculation of the MR image data set from a comparison between the three-dimensional MR volume data set and the MR image data set; and
calculating a deformed three-dimensional MR volume data set by applying the transformation to the three-dimensional MR volume data set.

4. The method as claimed in claim 3, comprising:
in response to the determination that the location of the central beam has changed, calculating each of (i) the transformation of the movement between the recording of the three-dimensional MR volume data set and the calculation of the MR image data set, and (ii) the deformed three-dimensional MR volume data set.

5. The method as claimed in claim 3, wherein the deformed three-dimensional MR volume data set identifies subject movement from a time period between the recording of the MR image data set and the calculation of the changed MR image data set.

6. The method as claimed in claim 5, wherein the act of determining the radiation dose for the irradiation in predetermined regions of the subject comprises using the deformed three-dimensional MR volume data set for determining the radiation dose.

7. The method as claimed in claim 1, comprising:
determining a position of an organ in the subject that is located inside or outside of the target volume,
wherein the MR image data set is calculated such that the organ is contained at least partially within the MR image data set.

8. The method as claimed in claim 1, comprising:
determining that a limit dose is exceeded in defined anatomical regions of the subject that are located inside or outside of the target volume; and
in response to the determination that the limit dose has been exceeded, automatically switching the irradiation off.

9. The method as claimed in claim 1, comprising:
determining the location of the central beam using control data, with which the location of the central beam is controlled by the radiation therapy apparatus.

10. The method as claimed in claim 1, wherein the act of continuously determining the location of the central beam relative to the subject comprises continuously determining the location of the central beam using image data acquired by a camera.

11. The method as claimed in claim 1, wherein the act of continuously determining the location of the central beam relative to the subject comprises continuously determining the location of the central beam using defined markings that occupy a defined location relative to the central beam in MR image data.

12. The method as claimed in claim 1, further comprising:
calculating a transformation of the movement between the recording of the three-dimensional MR volume data set and the calculation of the MR image data set from a comparison between the three-dimensional MR volume data set and the movement information of the subject;
calculating a deformed three-dimensional MR volume data set by applying the transformation to the three-dimensional MR volume data set; and
calculating a deformed MR image data set from the MR image data set and the movement information of the subject.

13. The method as claimed in claim 12, wherein the deformed MR image data set contains a plurality of two-dimensional slices, and
wherein the act of calculating the deformed three-dimensional volume data set comprises:
calculating the deformed three-dimensional volume data set using the deformed MR image data set and the three-dimensional MR volume data set.

14. A combined system therapy and imaging system, comprising:
a radiation therapy apparatus;
a magnetic resonance (MR) imaging apparatus;
a control computer configured to:
operate the MR imaging apparatus to acquire a three-dimensional MR volume data set prior to irradiation of the subject, the three-dimensional MR volume data set containing a target volume for irradiation of the subject with a radiation beam;
determine movement information of the subject;
continuously determine a location of a central beam of the radiation beam relative to the subject;
determine that the location of the central beam has changed during the irradiation of the subject;
calculate during the irradiation of the subject an MR image data set comprising two-dimensional MR slices that are positioned substantially perpendicular to the central beam
in response to the determination that the location of the central beam has changed, calculating, via the combined system during the irradiation of the subject, a changed MR image data set comprising two-dimensional MR slices that are substantially perpendicular to the central beam,
wherein the MR image data set and the changed MR data set are each respectively calculated during the irradiation of the subject without using a recorded MR data set in addition to the three-dimensional MR volume data set that was acquired prior to the irradiation of the subject by (i) using the movement information, and (ii) calculating, from the three-dimensional MR volume data set of the subject recorded prior to the irradiation of the subject, the two-dimensional MR slices of the changed MR image data set;

determine a radiation dose for the irradiation in predetermined regions of the subject using the MR image data set and the changed MR image data set; and control the irradiation using the determined radiation dose.

15. A non-transitory, computer-readable data storage medium encoded with programming instructions and being loaded into a computer system of a combined system comprising a radiation therapy apparatus and a magnetic resonance (MR) imaging apparatus, the programming instructions, when executed by the computer system, causing the computer system to:

operate the MR imaging apparatus to acquire a three-dimensional MR volume data set prior to irradiation of the subject, the three-dimensional MR volume data set containing a target volume for irradiation of the subject with a radiation beam;

determine movement information of the subject;

continuously determine a location of a central beam of the radiation beam relative to the subject;

determine that the location of the central beam has changed during the irradiation of the subject;

calculate during the irradiation of the subject an MR image data set comprising two-dimensional MR slices that are positioned substantially perpendicular to the central beam;

in response to the determination that the location of the central beam has changed, calculating, via the combined system during the irradiation of the subject, a changed MR image data set comprising two-dimensional MR slices that are substantially perpendicular to the central beam, wherein the MR image data set and the changed MR data set are each respectively calculated during the irradiation of the subject without using a recorded MR data set in addition to the three-dimensional MR volume data set that was acquired prior to the irradiation of the subject by (i) using the movement information, and (ii) calculating, from the three-dimensional MR volume data set of the subject recorded prior to the irradiation the subject, the two-dimensional MR slices of the changed MR image data set;

determine a radiation dose for the irradiation in predetermined regions of the subject using the MR image data set and the changed MR image data set; and control the irradiation using the determined radiation dose.

16. The method as claimed in claim 1, wherein the two-dimensional MR slices of the MR image data set and the changed MR image data set, respectively, are each elastically deformed on based upon the movement information in accordance with a calculated elastic deformation of the three-dimensional MR volume data set.

* * * * *